United States Patent [19]

Sawada et al.

[11] Patent Number: 5,260,435

[45] Date of Patent: Nov. 9, 1993

[54] DERIVATIVE OF NAPHTHALOCYANINE CONTAINING PERFLUOROALKYL GROUP, PROCESS FOR PREPARING THE SAME AND OPTICAL RECORDING MEDIUM

[75] Inventors: Hideo Sawada; Motohiro Mitani, both of Tsukuba; Masaharu Nakayama, Tsuchiura; Yoshii Morishita; Mitsuo Katayose, both of Hitachi; Tadashi Okamoto, Joyo; Nobuyuki Hayashi, Hitachi, all of Japan

[73] Assignees: Nippon Oil and Fats Co., Ltd.; Hitachi Chemical Co., Ltd., both of Tokyo, Japan

[21] Appl. No.: 838,781

[22] PCT Filed: Mar. 5, 1991

[86] PCT No.: PCT/JP91/00292

§ 371 Date: Mar. 18, 1992

§ 102(e) Date: Mar. 18, 1992

[87] PCT Pub. No.: WO92/01689

PCT Pub. Date: Feb. 6, 1992

[30] Foreign Application Priority Data

Jul. 23, 1990 [JP] Japan ............... 2-192870
Feb. 21, 1991 [JP] Japan ............... 3-027401
Feb. 26, 1991 [JP] Japan ............... 3-031056

[51] Int. Cl.$^5$ ............................ C07B 47/30
[52] U.S. Cl. .................... 540/122; 540/128; 540/140

[58] Field of Search ............ 540/122, 128, 136, 140

[56] References Cited

FOREIGN PATENT DOCUMENTS 0277039 8/1988 European Pat. Off. .
61-186384 8/1986 Japan .

OTHER PUBLICATIONS

CA:106: 166306m "Laser-Sensitive" optical recording medium (1987).
Hayashida et al., *Chemistry Letters*, The Chemistry Society of Japan, pp. 2137–2140, 1990.
Wheller et al., *J. Am. Chem. Soc.*, 106:7404–7410, 1984.
Kovshev et al., *Zh. Obshch. Khim.*, 42:696–699, 1972.
Firey et al., *J. Am. Chem. Soc.*, 110:7626–7630, 1988.

*Primary Examiner*—Thurman K. Page
*Assistant Examiner*—Jyothsna Venkat
*Attorney, Agent, or Firm*—Darby & Darby

[57] ABSTRACT

A derivative of naphthalocyanine containing a perfluoroalkyl group and having a particular structure for ensuring excellent weather-proof properties, extremely high solubility in various solvents and capability of forming a film, and an optical recording medium prepared by using the derivative and capable of recording while using a focused beam of a semiconductor laser or the like. The derivative of naphthalocyanine containing a perfluoroalkyl group may be prepared by reacting a perfluoroalkanoyl peroxide having a particular structure with a naphthalocyanine.

2 Claims, No Drawings

DERIVATIVE OF NAPHTHALOCYANINE CONTAINING PERFLUOROALKYL GROUP, PROCESS FOR PREPARING THE SAME AND OPTICAL RECORDING MEDIUM

FIELD OF ART

The present invention relates to a novel derivative of naphthalocyanine containing a perfluoroalkyl group, and particularly to a process for preparing such an industrially useful derivative of naphthalocyanine containing a perfluoroalkyl group and an optical recording medium capable of recording information using a focused beam of a semiconductor laser.

BACKGROUND TECHNOLOGY

Cyanine compounds have hitherto been known to be used as absorbents for the rays within the near infrared and infrared regions, but the cyanine compounds are generally unstable to light and heat. On the other hand, since naphthalocyanine compounds are extremely stable to light, heat and humidity and excellent in toughness, they attract attention to be used as polymer materials for preparing films or thin membranes having high performance characteristics by blending with various dyes, pigments, optical information recording media, photoelectric conversion media, electron photographic sensors and polymer materials.

However, naphthalocyanine compounds are generally scarcely soluble in organic solvents and thus difficulties are encountered in forming films thereof by ordinary film forming processing. Accordingly, there is an earnest demand for a compound having excellent properties comparable to naphthalocyanine compounds and capable of forming a film, and there is also an earnest demand for the development of a process for preparing such a compound on an industrial scale.

Also already proposed and applied for practical use as optical recording media are recording media each having an inorganic recording film layer made of a low melting point metal such as Te, Te alloys or Bi alloys.

However, production efficiency of such a recording medium having an inorganic recording film layer is low since the recording film layer must be formed by vacuum evaporation, or sputtering and there is a problem in recording density since the thermal conductivity of the recording film layer is high. Furthermore, since a harmful metal is used to prepare a recording medium having such an inorganic recording film layer, it is essential to overcome the problems concerning operation environment and waste water disposal.

In order to solve these problems, various proposals have been made to use phthalocyanine pigments which are known as blue to green pigments and excellent in stability as materials for optical recording media, specific examples being copper phthalocyanine, lead phthalocyanine, titanium phthalocyanine, vanadyl phthalocyanine and tin phthalocyanine (Unexamined Japanese Patent Publication Nos. 36490/1983 and 11292/1984). However, these pigments are inferior in matching with the semiconductor lasers, which are commonly used as the recording lasers at the present day, having oscillation wavelengths at approximately 780 to 830 nm, since they have maximum absorption wavelengths in the vicinity of 700 nm.

Under these circumstances, although there is proposed a process in which the absorption wavelengths are shifted to the long wavelenth region by means of processing with organic solvents or heating treatment, such a process has not yet been applied for practical use since these metal phthalocyanine pigments are scarcely soluble in organic solvents, in addition to complicated processing steps, so that it is impossible to form a thin film on a substrate made of a thermoplastic resin substrate, such as polycarbonate by coating solutions thereof and it is inevitable to use vacuum evaporation coating or sputtering technique.

In order to solve various problems described above, an optical recording medium has been proposed, in which a soluble organic pigment is used to form a recording film layer on a substrate by coating. More specifically, developed and applied for practical use is an optical recording medium which is formed by spin coating an organic pigment which has an absorption wavelength within the oscillation wavelengths of semiconductor lasers and is soluble in organic solvents, more specific examples of such a pigment being dithiol-metal complexes, polymethine pigments, squaraine pigments, cyanine pigments and naphthoquinone pigments.

However, the optical recording media containing the aforementioned organic pigments have disadvantages that they are poor in durability and weather-proof properties and low in reflectivity needed for reproducing the informations. Also known in the art as pigments which are excellent in durability and weather-proof properties and have absorption peaks vicinal to 800 nm are naphthalocyanines having the tetraazaporphyrin skeletal structure similar to phthalocyanine pigments (Inorg. Chim. Acta., 44, L209 (1980); Zh. Obshch. Khim., 42(3), 696 (1972)). However, these known naphthalocyanines and metal salts thereof have a disadvantage that they are more scarcely soluble in general organic solvents than the corresponding phthalocyanine compounds.

In recent years, various investigations have been made to improve the solubility of naphthalocyanines and metal salts thereof in organic solvents (Specification of U.S. Pat. No. 4,492,750, Specification of U.S. Pat. No. 4,725,525, Unexamined Japanese Patent Publication No. 25886/1986, J. Am. Chem. Soc., 106, 7404 (1984), Unexamined Japanese Patent Publication No. 177287/1986, Unexamined Japanese Patent Publication No. 177288/1986 and Unexamined Japanese Patent Publication No. 184565/1985), and it has been known that aromatic hydrocarbon solvents and halogenated solvents may be used as the organic solvents for dissolving these compounds. However, since the solubilities of these compounds, for example, in saturated hydrocarbon solvents and alcohol solvents are extremely low, there arises a problem that a layer resisting to solvent must be formed on a polymethyl methacrylate or polycarbonate substrate when a recording film layer is formed on such a substrate.

Further known to improve the general solubilities of naphthalocyanines is a method in which plural substituting groups having long chain alkyl groups are introduced. However, if the solubility is improved by such a method, the melting point of the resultant product is lowered to induce a disadvantage that the recording film layer tends to melt when the optical recording medium is subjected to reproduction for a long time as well as during the recording step. Accordingly, there is a demand for the development of a method for solubilizing the naphthalocyanine compounds in saturated hydrocarbon solvents and alcohol solvents without lowering the melting points thereof.

In general, naphthalocyanines have a disadvantage that the once formed amorphous recording film is crystallized gradually under a high temperature and high humidity condition to lose the recorded information since they have large planar χ-conjugated bonds to have extreme association force between individual molecules. Accordingly, there arises a problem that such crystallization must be suppressed.

Accordingly, an object of this invention is to provide a novel derivative of naphthalocyanine containing a perfluoroalkyl group, which is excellent in weatherability, high in solubility in various organic solvents and capable of forming a film, and to provide a process for preparing the same.

Another object of this invention is to provide an industrially useful process for preparing a derivative of naphthalocyanine containing a perfluoroalkyl group at high yield without using any special apparatus and reaction catalyst within a short time.

A further object of this invention is to provide an optical recording medium which has high sensitivity and durability including resistance to reproducing laser beam, resistance to environment and resistance to crystallization.

DISCLOSURE OF THE INVENTION

According to the present invention, there is provided a derivative of naphthalocyanine containing a perfluoroalkyl group represented by the following general formula (IV) of:

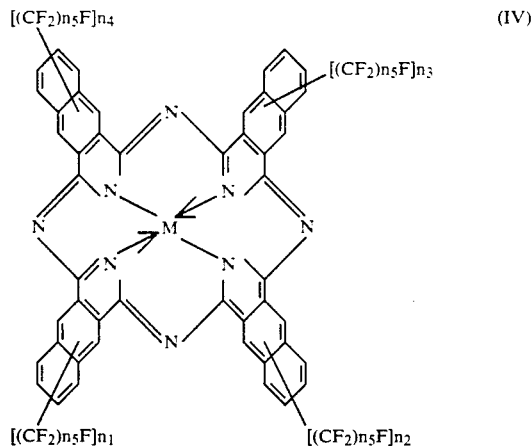

(wherein M stands for $H_2$, copper, $(R)_3SiO-Si-OSi(R)_3$ or $[F(CF_2)_{n5}\text{---}(R)_2SiO-Si-OSi(R)_3$ where R is an alkyl group having 1 to 10 carbon atoms; $n_1$, $n_2$, $n_3$ and $n_4$ each stand for an integer of from 0 to 2 and $n_5$ stands for an integer of 1 to 10; $n_1+n_2+n_3+n_4 \neq 0$ when M is $H_2$, copper or $(R)_3SiO-Si-OSi(R)_3$.

Meantime, both of the naphthalocyanine derivative containing a perfluoroalkyl group represented by the general formula (IV) wherein M is $H_2$, and the naphthalocyanine derivative containing a perfluoroalkyl group represented by the general formula (IV) wherein M are other than $H_2$ are novel compounds.

The present invention further provides an optical recording medium wherein a recording film layer mainly composed of a naphthalocyanine derivative containing a perfluoroalkyl group represented by the general formula (IV) is formed on a substrate. It is preferred to use, as a main component of the recording film layer, a single or mixed derivative of naphthalocyanine containing a perfluoroalkyl group and represented by the aforementioned general formula (IV) wherein M is other than $H_2$ and copper or a mixture of a single or mixed derivative of naphthalocyanine containing a perfluoroalkyl group and represented by the formula (IV) wherein M is other then $H_2$ and copper with a single or mixed derivative of naphthalocyanine containing a perfluoroalkyl group represented by the aforementioned general formula (IV) wherein M is $H_2$ or copper.

The present invention further provides a process for preparing a derivative of naphthalocyanine containing a perfluoroalkyl group represented by the aforementioned general formula (IV), comprising reacting a naphthalocyanine with a perfluoroalkanoyl peroxide represented by the following general formula (III) of:

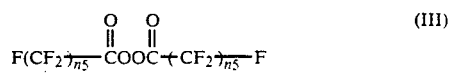

(wherein $n_5$ stands for an integer of from 1 to 10.)

BEST EMBODIMENT FOR THE PRACTICE OF THE INVENTION

The present invention will be described more in detail in the following description.

The derivatives of naphthalocyanine containing a perfluoroalkyl group, provided by this invention, is represented by the following general formula (IV) of:

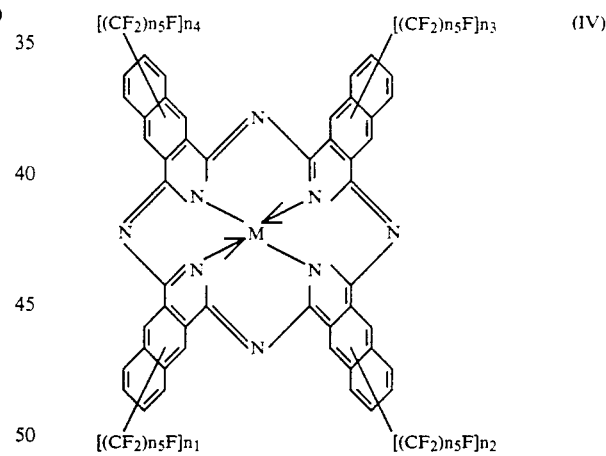

In the formula, M stands for $H_2$, copper, $(R)_3SiO-Si-OSi(R)_3$ or $[F(CF_2)_{n5}\text{---}(R)_2SiO-Si-OSi(R)_3$ where R is an alkyl group having 1 to 10 carbon atoms; $n_1$, $n_2$, $n_3$ and $n_4$ each stand for an integer of from 0 to 2 and $n_5$ stands for an integer of 1 to 10; and $n_1+n_2+n_3+n_4 \neq 0$ when M is $H_2$, copper or $(R)_3SiO-Si-OSi(R)_3$. It becomes difficult to prepare the derivatives if $n_5$ is more than 10, either one of $n_1$, $n_2$, $n_3$ and $n_4$ is more than 3 or R is an alkyl group having more than 11 carbon atoms. Meantime, both of the naphthalocyanine derivative containing a perfluoroalkyl group represented by the general formula (IV) wherein M is $H_2$ (hereinafter referred to as Naphthalocyanine Derivative A), and the naphthalocyanine derivatives each containing a perfluoroalkyl group represented by the general formula (IV) wherein M are other than $H_2$ (hereinafter referred to as Naphthalocyanine Derivatives B) are novel compounds.

It is preferred that the perfluoroalkylation ratio of the derivatives of naphthalocyanine each containing a perfluoroalkyl group, according to this invention, ranges from 100 to 800% for the aforementioned Naphthalocyanine Derivative A and ranges from 100 to 900% for the aforementioned Naphthalocyanine Derivatives B. When one perfluoroalkyl group is introduced per one naphthalocyanine molecule, it will be described that the perfluoroalkylation ratio is 100%.

Preferable derivatives of naphthalocyanine each containing a perfluoroalkyl group and represented by the aforementioned general formula (IV) include perfluoromethylated naphthalocyanine, perfluoroethylated naphthalocyanine, perfluoropropylated naphthalocyanine, perfluorobutylated naphthalocyanine, perfluoropentylated naphthalocyanine, perfluorohexylated naphthalocyanine, perfluoroheptylated naphthalocyanine, perfluorooctylated naphthalocyanine, perfluorononylated naphthalocyanine, perfluorodecylated naphthalocyanine, tetraperfluoroethyl naphthalocyanine, tetraperfluoropropyl naphthalocyanine, perfluoromethylated copper naphthalocyanine, perfluoroethylated copper naphthalocyanine, perfluoropropylated copper naphthalocyanine, perfluorobutylated copper naphthalocyanine, perfluoropentylated copper naphthalocyanine, perfluorohexylated copper naphthalocyanine, perfluoroheptylated copper naphthalocyanine, perfluorooctylated copper naphthalocyanine, perfluorononylated copper naphthalocyanine, perfluorodecylated copper naphthalocyanine, tetraperfluorobutyl copper naphthalocyanine, diperfluoropentyl copper naphthalocyanine, diperfluorohexyl copper naphthalocyanine, diperfluoroheptyl copper naphthalocyanine, diperfluorooctyl copper naphthalocyanine, diperfluorononyl copper naphthalocyanine, diperfluorodecyl copper naphthalocyanine, pentafluoropropyl copper naphthalocyanine, perfluoropropyldihexylsiloxy-trihexylsiloxy-silicon naphthalocyanine, perfluoropropylated (perfluoropropyl-dihexylsiloxy-trihexylsiloxy-silicon) naphthalocyanine, perfluoropropylated (perfluoropropyl-dihexylsiloxy-trihexylsiloxy-silicon) naphthalocyanine, perfluoropropylated (perfluoropropyldipropylsiloxy-tripropylsiloxy-silicon) naphthalocyanine, perfluoropropylated (perfluoropropyldipropylsiloxy-tripropylsiloxy-silicon) naphthalocyanine, perfluoropropylated (perfluoropropyldiethylsiloxy-triethylsiloxy-silicon) naphthalocyanine, tetraperfluoropropyl-bis(trimethylsiloxy) silicon naphthalocyanine, diperfluoropropyl-bis(trimethylsiloxy) silicon naphthalocyanine, diperfluorobutyl-bis(trimethylsiloxy) silicon naphthalocyanine, diperfluoropentyl-bis(trimethylsiloxy) silicon naphthalocyanine, diperfluorohexyl-bis(trimethylsiloxy) silicon naphthalocyanine, diperfluoroheptyl-bis(trimethylsiloxy) silicon naphthalocyanine, perfluorooctyl-bis(trimethylsiloxy) silicon naphthalocyanine, perfluorononyl-bis(trimethylsiloxy) silicon naphthalocyanine, perfluorodecyl-bis(trimethylsiloxy) silicon naphthalocyanine, tetraperfluoroethyl-bis(triethylsiloxy) silicon naphthalocyanine, tetraperfluoropropyl-bis(triethylsiloxy) silicon naphthalocyanine, perfluoropropyl-bis(triethylsiloxy) silicon naphthalocyanine, perfluorobutyl-bis(triethylsiloxy) silicon naphthalocyanine, perfluoropentyl-bis(triethylsiloxy) silicon naphthalocyanine, perfluorohexyl-bis(triethylsiloxy) silicon naphthalocyanine, perfluoroheptyl-bis(triethylsiloxy) silicon naphthalocyanine, diperfluoroethyl-bis(tripropylsiloxy) silicon naphthalocyanine, perfluoropropyl-bis(tripropylsiloxy) silicon naphthalocyanine, diperfluoropropyl-bis(tripropylsiloxy) silicon naphthalocyanine, triperfluoropropyl-bis(tripropylsiloxy) silicon naphthalocyanine, perfluorobutyl-bis(tripropylsiloxy) silicon naphthalocyanine, perfluoroethyl-bis(tributylsiloxy) silicon naphthalocyanine, diperfluoroethyl-bis(tributylsiloxy) silicon naphthalocyanine, tetraperfluoroethyl-bis(tributylsiloxy) silicon naphthalocyanine, perfluoropropyl-bis(tributylsiloxy) silicon naphthalocyanine, diperfluoropropyl-bis(tributylsiloxy) silicon naphthalocyanine, tetraperfluoropropyl-bis(tributylsiloxy) silicon naphthalocyanine, perfluoropropyldihexylsiloxy-trihexylsiloxy-silicon naphthalocyanine, diperfluoropropyl(perfluoropropyldihexylsiloxy-trihexylsiloxy-silicon) naphthalocyanine, triperfluoropropyl(perfluoro-propyldipropylsiloxy-tripropylsiloxy-silicon) naphthalocyanine, diperfluoropropyl(perfluoropropyl-diethylsiloxy-triethylsiloxy-silicon) naphthalocyanine, perfluoropropyl(-perfluoropropyldiethylsiloxy-triethylsiloxy-silicon) naphthalocyanine, diperfluoroethyl-bis(trihexylsiloxy) silicon naphthalocyanine, triperfluoroethyl-bis(trihexylsiloxy) silicon naphthalocyanine, perfluoropropyl-bis(trihexylsiloxy) silicon naphthalocyanine, diperfluoropropyl-bis(trihexylsiloxy) silicon naphthalocyanine, tetraperfluoropropyl-bis(trihexylsiloxy) silicon naphthalocyanine, perfluorohexyl-bis(trihexylsiloxy) silicon naphthalocyanine, perfluoromethyl-bis(trihexylsiloxy) silicon naphthalocyanine, perfluoroethyl-bis(trihexylsiloxy) silicon naphthalocyanine, perfluoropropyl-bis(trihexylsiloxy) silicon naphthalocyanine, perfluorobutyl-bis(trihexylsiloxy) silicon naphthalocyanine, perfluoropentyl-bis(trihexylsiloxy) silicon naphthalocyanine and perfluorohexyl-bis(trihexylsiloxy) silicon naphthalocyanine. Meanwhile, in the illustrated derivatives of naphthalocyanine each containing a perfluoroalkyl group, "perfluoroalkylation" such as "perfluoropropylation" means that a perfluoroalkyl group represented by $[(CF_2)_{n_4 5} F]_{n_4}$ (wherein $n_4$ and $n_5$ are the same as $n_4$ and $n_5$ defined in the aforementioned general formula (IV) is coupled to at least one of six positions of the naphthalene ring present in the aforementioned general formula (IV) at which such a group may be coupled. However, when M in the aforementioned general formula (II) is $[F(CF_2)_{n_5}(R)_2SiO-Si-OSi(R)_3$, it is not always essential that a perfluoroalkyl group is coupled to the naphthalene ring since a perfluoroalkyl group is already present in M.

The process for preparing a derivative of naphthalocyanine represented by the aforementioned general formula (IV), according to this invention, is characterized in that a particular perfluoroalkanoyl peroxide is reacted with any of naphthalocyanines.

The perfluoroalkanoyl peroxides, which are used as a feed component in the process of this invention, may be represented by the following general formula (III) of:

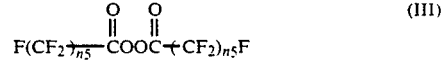

In the formula set forth above, $n_5$ stands for an integer of from 1 to 10. $n_5$ must be within the range as defined above, since the solubility of the peroxides in a solvent is lowered if $n_5$ exceeds 10 so that handling thereof in reaction becomes difficult. Specific examples of the perfluoroalkanoyl peroxides represented by the aforementioned general formula (III) include bis(perfluoroacetyl) peroxide, bis(perfluoropropionyl) peroxide, bis(perfluorobutyryl) peroxide, bis(perfluoropentanoyl) peroxide, bis(perfluorohexanoyl) peroxide, bis(perfluoroheptanoyl) peroxide, bis(perfluorooctanoyl) peroxide, bis(perfluoropelargonyl) peroxide, bis(perfluorodecanoyl) peroxide and bis(perfluoroundecanoyl) peroxide.

Specific examples of the naphthalocyanines which may be reacted with the aforementioned perfluoroalkanoyl peroxides in the process of this invention include naphthalocyanine, copper naphthalocyanines, and silicon naphthalocyanines represented by the following general formula (VII) of:

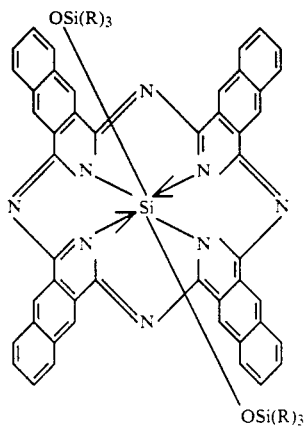

(wherein R stands for an alkyl group having 1 to 10 carbon atoms.)

Specific examples of the silicon naphthalocyaines include bis(trimethylsiloxy) silicon naphthalocyanine, bis(triethylsiloxy) silicon naphthalocyanine, bis(tripropylsiloxy) silicon naphthalocyanine, bis(tributylsiloxy) silicon naphthalocyanine, bis(tripentylsiloxy) silicon naphthalocyanine, bis(trihexylsiloxy) silicon naphthalocyanine, bis(triheptylsiloxy) silicon naphthalocyanine, bis(trioctylsiloxy) silicon naphthalocyanine, bis(trinonylsiloxy) silicon naphthalocyanine and bis(tridecylsiloxy) silicon naphthalocyanine.

It is preferred that the naphthalocyanines and the perfluoroalkanoyl peroxides are charged in a molar ratio of from 1:0.2 to 20, particularly 1:0.5 to 10. If the molar ratio of charged perfluoroalkanoyl peroxide is less than 0.2, the yield of the produced derivative of naphthalocyanine containing an alkyl group is lowered and the ratio of perfluoroalkyl group introduced in the produced naphthalocyanine is reduced, whereas it is not preferable that the ratio of charged perfluoroalkanoyl peroxide exceeds 20, since sole decomposition of perfluoroalkanoyl peroxide becomes predominant to make the process impertinent for industrial preparation process.

The reaction between the perfluoroalkanoyl peroxides and the naphthalocyanines may proceed under atmospheric pressure, preferably at a reaction temperature of from $-20°$ to $150°$ C., particularly preferably from $0°$ to $100°$ C., for 0.5 to 20 hours, whereby derivatives of naphthalocyanine each containing an introduced perfluoroalkyl group, such as $CF_3-$, $F(CF_2-)_2$, $F(CF_2-)_3$, $F(CF_2-)_4$, $F(CF_2-)_5$, $F(CF_2-)_6$, $F(CF_2-)_7$, $F(CF_2-)_8$, $F(CF_2-)_9$, and $F(CF_2-)_{10}$, may be prepared. The reaction time becomes too long if the reaction temperature is lower than $-20°$ C., whereas the pressure during reaction becomes disadvantageously high to arise difficulty in reaction operation if the reaction temperature is higher than $150°$ C.

When the perfluoroalkanoyl peroxides are reacted with the naphthalocyanines according to this invention, the reaction may proceed in the presence of a solvent, for example a halogenated aliphatic compound, for easy handling of the perfuloroalkanoyl peroxide. The most preferable halogenated aliphatic solvent from the industrial point of view is 1,1,2-trichloro-1,2,2-trifluoroethane.

The reaction products prepared by this invention may be purified through known processes including column chromatography.

The optical recording medium of this invention is characterized in that the main component of the recording film layer formed on a substrate is any of the derivatives of naphthalocyaines (hereinafter referred to as Naphthalocyanine Derivatives C) represented by the aforementioned general formula (IV), more preferably the main component is selected from the derivatives of naphthalocyanines (hereinafter referred to as Naphthalocyanine Derivatives D) included in the Naphthalocyanine Derivatives C wherein M in the formula is other than $H_2$ and copper, or a mixture of the Naphthalocyanine Derivatives D with any of the derivatives of naphthalocyanine (hereinafter referred to as Naphthalocyanine Derivatives E) wherein M in the formula is $H_2$ or copper.

Since each of the derivatives of naphthalocyanine according to this invention has perfluoroalkyl group, the association power between individual molecules is lowered, as compared to the unsubstituted naphthalocyanine, so that the solubility thereof in a solvent is remarkably improved. Meanwhile, although the solubility may be improved by the introduction of an alkyl group into naphthalocyanine, improvement in solubility is appreciably improved by the introduction of a perfluoroalkyl group when the product prepared by the introduction of a perfluoroalkyl group having a certain number of carbon atom is compared to the product prepared by the introduction of an alkyl group having the same number of carbon atoms. In general, the melting points of naphthalocyanines are lowered gradually with the increase in number of the introduced substituting groups and as described above, since the products prepared by the introduction of perfluoroalkyl groups have the solubilities equivalent to or higher than the solubilities of the products prepared by the introduction of alkyl groups even when the number of introduced substituting groups is smaller, the aforementioned derivatives of naphthalocyanine are compounds which are improved in solubility and suppressed in attendant lowering of melting point. Particularly, since the aforementioned Naphthalocyanine Derivatives D are introduced with perfluoroalkyl groups which are intensive in steric repelling force, they are particularly preferable for use as the main component in the recording film layer without appreciable reduction in reflectivity due to intermolecular association. On the other hand, the aforementioned Naphthalocyanine Derivatives E have the tendency that the reflectivities and the absorbancies (100 — Reflectivity — Percent Transmission) thereof are lower as compared to those of the aforementioned Naphthalocyanine Derivatives D, so that the stability against the reproducing laser beam can be improved by using a mixture of the Naphthalocyanine Derivatives D with the Naphthalocyanine Derivatives E as the main component for forming the recording film layer by the utilization of the aformentioned characteristics. It is preferable that the mixing ratio of the aforementioned Naphthalocyanine Derivatives D and the Naphthalocyanine Derivatives E ranges within 10:1 to 5 by weight, particularly preferably within 10:1 to 3 by weight. Meantime, preferable examples of the aforementioned derivatives of naphthalocyanine include those specifically represented by the general formula (IV) set forth above, and in principle they may be used singly or in the form of a mixture.

In order to form a recording film layer on a substrate to prepare an optical recording medium in the present invention, the aforementioned derivatives of naphthalocyanine may be dissolved, for example, in an appropriate organic solvent and coated by spray coating, spin coating or other processes to be carried on the substrate. Suitable materials for the substrate include thermoplastic resins such as polyvinyl chloride resins, acrylic resins, polyolefin resins, polycarbonate resin and polyvinyl acetal resin; thermosetting resins such as epoxy resins, unsaturated polyester resins and vinyl ester resins; and glass and metals. For instance, when recording and reproduction are effected by irradiating a laser beam from the substrate side, the substrate must be transparent in the wavelength range of the used laser beam. The substrate may have a construction composed of a flat plate molded from the aforementioned materials and a photocured resin layer laminated on the flat plate, the photocured resin layer having a surface on which a guide track pattern is transferred.

For instance, when the material for the substrate is a thermoplastic resin, a solvent which does not damage the pre-groove or pre-pit formed in the substrate may be used for forming the aforementioned recording film layer, the examples being saturated hydrocarbon solvents such as pentane, hexane, heptane, octane, nonane, decane, cyclopentane, cyclohexane and cycloheptane; alcohol solvents such as methanol, ethanol, propanol, isopropyl alcohol, butanol, isobutyl alcohol and t-butyl alcohol; benzene, toluene, xylene, chlorobenzene, 1-chloronaphthalene, methylene chloride, chloroform, carbon tetrachloride, trichloroethane, diethyl ether, ethyleneglycol dimethyl ether, diethyleneglycol monomethyl ether, diethyleneglycol dimethyl ether, ethylbenzene, methyl ethyl ketone, acetone, methyl propyl ketone, cyclopentanone, cyclohexanone, acetone alcohol, diacetone alcohol, diisobutyl ketone, propylene oxide, furan, 1,3-dioxolan, acetate, dimethoxymethane, dimethoxypropane, diethoxymethane, 1,2-dimethoxypropane, 2,2-dimethoxypropane. 2-pentanone, 3-pentanone, 1,2-butylene oxide, n-butyl-2,3-epoxy propyl ether, carbon disulfide, diisopropyl ether, nitromethane, acetonitrile, 1,3-dicyanopropane, dioxane and ethyl acetate. These solvents may be used singly or in the form of a mixture.

The aforementioned recording film layer may be formed by applying each of the aforementioned derivatives of naphthalocyanine used as the main component of the recording film layer in the laminated structure or in the single layer structure. The aforementioned derivatives of naphthalocyanine may be used singly or in the form of a mixture, and each of them may be laminated or they may be mixed together and then used to form a single layer structure. The film thickness of the aforementioned recording film layer ranges preferably from 50 to 10000 Å, particularly preferably from 100 to 5000 Å.

A reflected light may be used for the optical reproduction of the recorded image stored in the aforementioned recording film layer. In order to raise the contrast in this step, a metal layer having a high reflectivity may be provided, if necessary, on the surface of the recording film layer opposite to the substrate when the image is written in and read out from the substrate side; or a metal layer having a high reflectivity may be provided between the substrate and the recording film layer when the image is written in and read out from the side opposite to the substrate, namely from the recording film layer side. As the metal having a high reflectivity, Al, Cr, Au, Pt and Sn may be used. Such a layer may be formed by the known thin film forming processes, such as vacuum evaporation, sputtering or plasma deposition, and the thickness thereof ranges preferably from 100 to 10000 Å.

In order to improve the smoothness of the surface of the aforementioned substrate, a uniform membrane of an organic polymer compound may be provided over the substrate. Commercially available polymers, such as polyesters or polyvinyl chloride, may be used as the organic polymer compound.

Furthermore, in order to improve the stability and protection properties of the recording film layer and further to lower the surface reflectivity to increase the sensitivity, a protection layer may be provided as an outermost ply of the recording film layer. Materials for forming such a protection layer include polyvinilidene chloride, polyvinyl chloride, copolymers of vinylidene chloride and acrylonitrile, polyvinyl acetate, polyimide, polymethyl methacrylate, polystyrene, polyisoprene, polybutadiene, polyurethane, polyvinyl butyral, fluorinated rubbers, polyesters, epoxy resins, silicone resins and cellulose acetate, these materials being used singly or in the form of a mixture. With the aim to reinforce the properties of such a protection layer, silicone oil, an antistatic agent or a cross-linking agent may be present in the layer, or plural protection layers may be provided. Such a protection layer may be formed, for example, by dissolving a material for forming the protection layer followed by coating, or by laminating a thin film for forming the protection layer. The thickness of the protection layer ranges preferably from 0.1 to 10 $\mu$m, particularly preferably from 0.1 to 2 $\mu$m.

The derivatives of naphthalocyanine each containing a perfluoroalkyl group, according to this invention, are novel compounds and are soluble in various organic solvents, so that they are useful as optical information recording media, photo-electric convertors, photosensitive materials for electron photography or polymer materials for blending with other polymers to form films or thin membranes having high performance characteristics.

Since particular perfluoroalkanoyl peroxides are used in the process of this invention, perfluoroalkyl groups can be directly and easily introduced into naphthalocyanines within a short period at high yield. In addition, since no reaction catalyst and no special device are used, it is extremely useful from the industrial standpoint of view.

Furthermore, since the optical recording medium according to this invention is formed by using, as the main component for forming the recording film layer, a compound excellent in resistance to laser beam used for reproduction, resistance to environment and resistance to crystallization and improved in solubility, it is high in sensitivity and excellent in durability and thus extremely useful when used, for example, as an optical disc, optical card or optical floppy.

EXAMPLES:

The present invention will be described more in detail by referring to Examples and Test Examples thereof in the following description, but it is to be noted here that the present invention is not restricted thereby.

EXAMPLE 1

0.5 g (0.7 mmol) of naphthalocyanine was added to and mixed with 10 g of 1,1,2-trichloro-1,2,2-trifluoroethane, to which added was 20 g of a solution of 1,1,2-trichloro-1,2,2-trifluoroethane containing 3.5 mmol of bis(perfluorobutyryl) peroxide to proceed the reaction at 40° C. for 5 hours. After the completion of reaction, 50 ml of chloroform was added to the reaction mixture, which was then filtered to remove unreacted materials. Then, the obtained chloroform layer was dried by using magnesium sulfate, and the product was purified through column chromatography. As a result, tetraperfluoropropyl naphthalocyanine represented by the following structural formula was obtained at a yield of 72%.

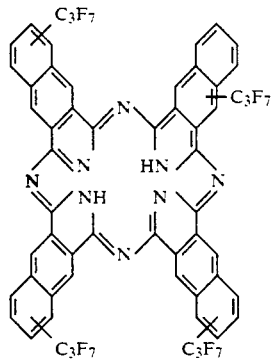

Meanwhile, the number of perfluoropropyl groups introduced in naphthalocyanine, i.e. the perfluoropropylation ratio, was determined by $^{19}F$—NMR while using benzotrifluoride as an internal standard indicator to find that the perfluoropropylation ratio was 400%, namely four perfluoropropyl groups were introduced per one molecule. The UV spectrum (Solvent used in Measurement: Chloroform), IR spectrum and $^{19}F$-NMR spectrum of the thus prepared perfluoropropylated naphtalocyanine are set forth below.

UV (nm): 261, 711.0, 729.0, 762.5.
IR (cm $^{-1}$): 1340 (CF$_3$), 1225 (CF$_2$).
$^{19}F$—NMR (CDCl$_3$, external, CF$_3$CO$_{02}$H) δ: $-8$ to $-10$ (CF$_3$), $-20$ to $-38$ (CF$_2$), $-46$ to $-58$ (CF$_2$).

EXAMPLE 2

Similar reaction and analyses were repeated as in Example 1, except that the charged quantity of bis(perfluorobutyryl) peroxide was changed to 2.8 mmol, to prepare perfluoropropylated naphthalocyanine at a yield of 69%. Meanwhile, the perfluoropropylation ratio was determined similarly to Example 1 to find that the perfluoropropylation ratio was 300%. The results of analyses of the thus prepared perfluoropropylated naphthalocyanine are set forth below.

UV (nm): 260, 592.5, 649.5, 669.0, 726.5.
IR (cm $^{-1}$): 1340 (CF$_3$), 1225 (CF$_2$).
$^{19}F$—NMR (CDCl$_3$, external, CF$_3$CO$_2$H) δ: $-8$ to $-10$ (CF$_3$), $-20$ to $-38$ (CF$_2$), $-46$ to $-58$ (CF$_2$).

EXAMPLE 3

Similar reaction and analyses were repeated as in Example 1, except that bis(perfluoropropionyl) peroxide was used in place of bis(perfluorobutyryl) peroxide, to prepare perfluoroethylated naphthalocyanine at a yield of 70%. Meanwhile, the perfluoroethylation ratio was determined similarly to Example 1 to find that the perfluoroethylation ratio was 400%. The results of analyses of the thus prepared perfluoroethylated naphthalocyanine are set forth below.

UV (nm): 670.0, 735.5.
IR (cm $^{-1}$): 1340 (CF$_3$), 1225 (CF$_2$).
$^{19}F$—NMR (CDCl$_3$, external, CF$_3$CO$_2$H) δ: $-8$ to $-10$ (CF$_3$), $-43$ to $-56$ (CF$_2$).

EXAMPLE 4

Similar reaction and analyses were repeated as in Example 1, except that bis(perfluoroheptanoyl) peroxide was used in place of bis(perfluorobutyryl) peroxide, to prepare perfluorohexylated naphthalocyanine at a yield of 65%. Meanwhile, the perfluorohexylation ratio was determined similarly to Example 1 to find that the perfluorohexylation ratio was 400%.

The results of analyses of the thus prepared perfluorohexylated naphthalocyanine are set forth below.

UV (nm): 260, 590.0, 670.8, 735.5.
IR (cm $^{-1}$): 1340 (CF$_3$), 1225 (CF$_2$).
$^{19}F$—NMR (CDCl$_3$, external, CF$_3$CO$_2$H) δ: $-5$ to $-10$ (3F), $-30.1$ to $-51.5$ (10F).

EXAMPLE 5

Similar reaction and analyses were repeated as in Example 1, except that bis(perfluorooctanoyl) peroxide was used in place of bis(perfluorobutyryl) peroxide, to prepare perfluoroheptylated naphthalocyanine at a yield of 65%. Meanwhile, the perfluoroheptylation ratio was determined similarly to Example 1 to find that the perfluoroheptylation ratio was 400%.

The results of analyses of the thus prepared perfluoroheptylated naphthalocyanine are set forth below.

UV (nm): 261, 670.8, 735.5.
IR (cm$^{-1}$): 1340 (CF$_3$), 1225 (CF$_2$).
$^{19}F$—NMR (CDCl$_3$, external, CF$_3$CO$_2$H) δ: $-5$ to $-10$(3F), $-30.1$ to $-51.5$(12F).

Example 6

Similar reaction and analyses were repeated as in Example 1, except that 0.2 g (0.26 mmol) of copper naphthalocyanine was used in place of naphthalocyanine and that the charged quantity of bis(perfluorobutyryl) peroxide was changed to 2.06 mmol, to prepare perfluoropropylated copper naphthalocyanine at a yield of 36%. Meanwhile, the perfluoropropylation ratio was determined similarly to Example 1 to find that the perfluoropropylation ratio was 490%. The results of analyses of the thus prepared perfluoropropylated copper naphthalocyanine are set forth below.

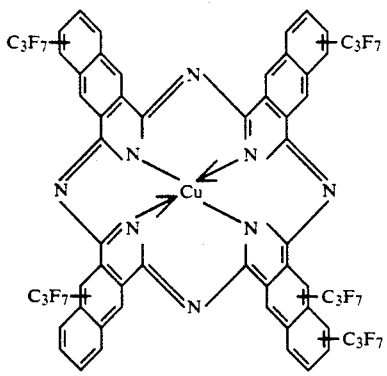

UV (nm): 668.5, 736.5.
IR (cm$^{-1}$): 1340 (CF$_3$), 1225 (CF$_2$).
$^{19}$F—NMR (CDCl$_3$, external, CF$_3$CO$_2$H) δ: −8 to −10 (CF$_3$), −20 to −38 (CF$_2$). −46 to −58 (CF$_2$).

EXAMPLE 7

Similar reaction and analyses were repeated as in Example 1, except that 0.5 g (0.37 mmol) of bis(trihexylsiloxy) silicon naphthalocyanine was used in place of naphthalocyanine and that the charged quantity of bis(perfluorobutyryl) peroxide was changed to 0.37 mmol, to prepare (perfluoropropyldihexylsiloxy-trihexylsiloxy-silicon) naphthalocyanine having the structure as set forth below at a yield of 46%.

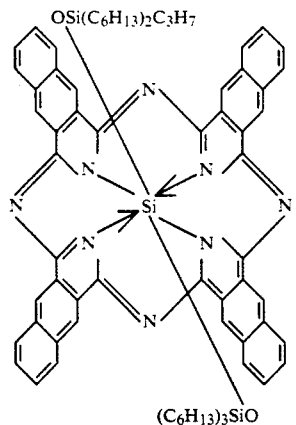

Meanwhile, the perfluoropropylation ratio was determined similarly to Example 1 to find that the perfluoropropylation ratio was 100%. The results of analyses and the melting point (mp) of the thus prepared perfluoropropyldihexylsiloxy-trihexylsiloxy-silicon naphthalocyanine are set forth below.
UV (nm): 779, 761
IR (cm$^{-1}$): 1340 (CF$_3$ ), 1225 (CF$_2$).
mp: 226° C. to 228° C. $^{19}$F—NMR (CDCl$_3$, external, CF$_3$CO$_2$H) δ: −2.8 (CF$_3$), −18.0 (CF$_2$), −45.7 (CF$_2$).

EXAMPLE 8

Similar reaction and analyses were repeated as in Example 1, except that 0.5 g (0.37 mmol) of bis(trihexylsiloxy) silicon naphthalocyanine was used in place of naphthalocyanine and that the charged quantity of bis(perfluorobutyryl) peroxide was changed to 1.42 mmol, to prepare diperfluoropropyl(perfluoropropyldihexlsiloxy-trihexylsiloxy-silicon) naphthalocyanine having the structure as set forth below at a yield of 46%.

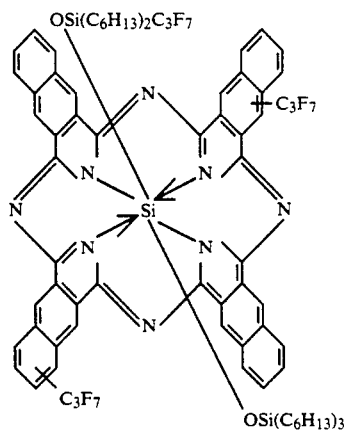

Meanwhile, the perfluoropropylation ratio was determined similarly to Example 1 to find that the perfluoropropylation ratio was 300%. The results of analyses of the thus prepared diperfluoropropyl(perfluoropropyldihexylsiloxy-trihexylsiloxy-silicon) naphthalocyanine are set forth below.
UV (nm): 771.
IR (cm$^{-1}$): 1340 (CF$_3$), 1225 (CF$_2$).
$^{19}$F—NMR (CDCl$_3$, external, CF$_3$CO$_2$H) δ: −2.5 to −5.5 (CF$_3$), −17.0 to −21.5 (CF2), −44.5 to −46.8 (CF$_2$).

EXAMPLE 9

Similar reaction and analyses were repeated as in Example 1, except that 0.5 g (0.46 mmol) of bis(tripropylsiloxy) silicon naphthalocyanine was used in place of naphthalocyanine and that the charged quantity of bis(perfluorobutyryl) peroxide was changed to 0.92 mmol, to prepare diperfluoropropyl(perfluoropropyldipropylsiloxy-tripropylsiloxy-silicon) naphthalocyanine having the structure as set forth below at a yield of 13%.

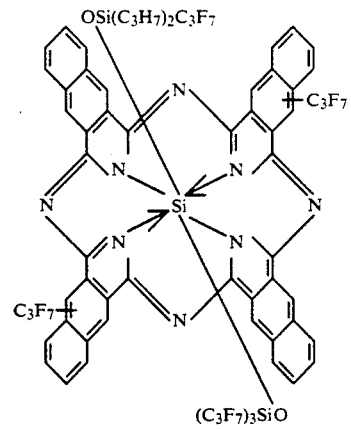

Meanwhile, the perfluoropropylation ratio was determined similarly to Example 1 to find that the perfluoropropylation ratio was 300%. The results of analyses of the thus prepared diperfluoropropyl(perfluoropropyldipropylsiloxy-tripropylsiloxy-silicon) naphthalocyanine are set forth below.
UV (nm): 764, 675.

IR (cm$^{-1}$): 1340 (CF$_3$), 1225 (CF$_2$).

$^{19}$F—NMR (CDCl$_3$, external, CF$_3$CO$_2$H) δ: −2.8 to −6.0 (CF$_3$), −17.2 to −19.0 (CF$_2$), −44.0 to −47.9 (CF$_2$).

EXAMPLE 10

Similar reaction and analyses were repeated as in Example 1, except that 0.5 g (0.46 mmol) of bis(tripropylsiloxy) silicon naphthalocyanine was used in place of naphthalocyanine and that the charged quantity of bis(perfluorobutyryl) peroxide was changed to 1.84 mmol, to prepare triperfluoropropyl(perfluoropropyldipropylsiloxy-tripropylsiloxy-silicon) naphthalocyanine having the structure as set forth below at a yield of 50%.

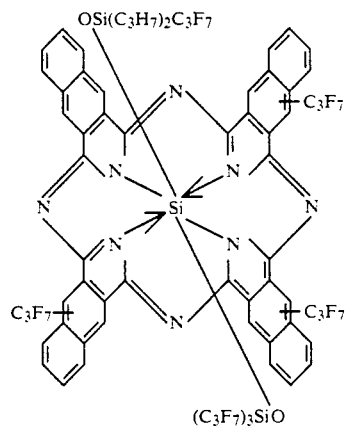

Meanwhile, the perfluoropropylation ratio was determined similarly to Example 1 to find that the perfluoropropylation ratio was 400%. The results of analyses of the thus prepared triperfluoropropyl(perfluoropropyl-dipropylsiloxy-tripropylsiloxy-silicon) naphthalocyanine are set forth below.

UV (nm): 773, 668, 613.

IR (cm$^{-1}$): 1340 (CF$_3$), 1225 (CF$_2$).

$^{19}$F—NMR (CDCl$_3$, external, CF$_3$CO$_2$H) δ: −2.8 to −6.5 (CF$_3$), −17.5 to −22.0 (CF$_2$), −45.0 to −52.0 (CF$_2$).

EXAMPLE 11

Similar reaction and analyses were repeated as in Example 1, except that 0.5 g (0.50 mmol) of bis(triethylsiloxy)silicon naphthalocyanine was used in place of naphthalocyanine and that the charged quantity of bis(perfluorobutyryl) peroxide was changed to 1.00 mmol, to prepare diperfluoropropyl(perfluoropropyldiethylsiloxy-triethylsiloxy-silicon) naphthalocyanine having the structure as set forth below at a yield of 13%.

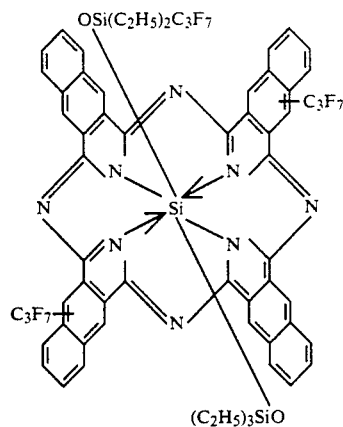

Meanwhile, the perfluoropropylation ratio was determined similarly to Example 1 to find that the perfluoropropylation ratio was 300%. The results of analyses of the thus prepared diperfluoropropyl(perfluoropropyl-dietylsiloxy-triethylsiloxy-silicon) naphthalocyanine are set forth below.

UV (nm): 767, 676.

IR (cm$^{-1}$): 1340 (CF$_3$), 1225 (CF$_2$).

$^{19}$F—NMR (CDCl$_3$, external, CF$_3$CO$_2$H) δ: −2.8 to −3.6 (CF$_3$), −18.2 to −20.5 (CF$_2$), −45.1 to −47.3 (CF$_2$).

EXAMPLE 12

0.5 g (0.37 mmol) of bis(trihexylsiloxy)silicon naphthalocyanine was added to and mixed with 20 ml of chloroform, to which added was 3.2 g of a solution of 1,1,2-trichloro-1,2,2-trifluoroethane containing 0.16 g (0.37 mmol) of bis(perfluorobutyryl) peroxide to proceed the reaction at 40° C. for 5 hours. After the completion of reaction, the reaction mixture was rinsed with a 0.5 wt % aqueous solution of sodium hydroxide and saturated aqueous saline. Then, the thus obtained chloroform layer was dried with magnesium sulfate, and the product was purified through column chromatography and further recrystallized by using a mixed solution of hexane ethanol. As a result, perfluoropropyl-bis(trihexylsiloxy) silicon naphthalocyanine represented by the following structural formula was prepared at a yield of 43%.

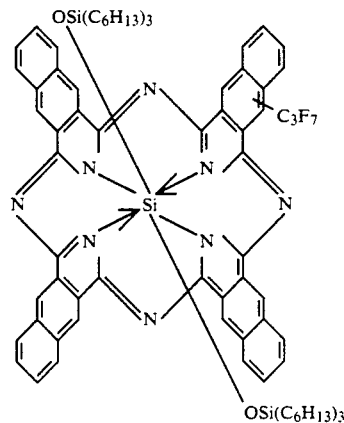

Meanwhile, the number of perfluoroalkyl groups introduced in the naphthalocyanine was determined by $^{19}$F—NMR while using o-chlorobenzotrifluoride as an internal standard liquid to find that the number of perfluoroalkyl groups was 1. The UV (Solvent Used in Measurement: Chloroform), IR, $^1$H—NMR, $^{19}$F—NMR and the melting point of the thus prepared perfluoropropyl-bis(trihexylsiloxy) silicon naphtalocyanine are shown below.

UV (nm): 781, 766.

IR (cm$^{-1}$) 1350 (CF$_3$), 1225 (CF$_2$).

$^1$H—NMR (CDCl$_3$)δ: 10.55 to 9.95 (m, 7H) 9.15 to 8.45 (m, 8H) 7.95 (b, 8H), 1.00 to 0.00 (m, 54H) −0.95 (b, 12H), −1.90 to −2.25 (m, 12H).

$^{19}$F—NMR (CDCl$_3$, external, CF$_3$CO$_2$H) δ: −2.8 (CF$_3$), −18.0 (CF$_2$), −45.7 (CF$_2$).

Melting Point (°C.): 226 to 228.

TEST EXAMPLE 1

Perfluoroalkylated naphthalocyanines prepared by Examples 1 to 12 were mixed with respective solvents as set forth in Table 1 to investigate the solubilities thereof. The solubility of naphthalocyanine was investigated as Comparative Example 1. The results are shown in Table 1.

TABLE 1

| Example No./Solvent | a | b | c | d | e | f | g | h | i | j |
|---|---|---|---|---|---|---|---|---|---|---|
| Example 1 | ⊚ | ⊚ | ⊚ | X | ○ | △ | ⊚ | ⊚ | △ | X |
| Example 2 | ⊚ | ⊚ | ⊚ | X | ○ | △ | ⊚ | ⊚ | △ | X |
| Example 3 | ⊚ | ⊚ | ⊚ | X | ○ | △ | ⊚ | ⊚ | △ | X |
| Example 4 | ⊚ | ⊚ | ⊚ | X | ○ | X | ⊚ | ⊚ | X | X |
| Example 5 | ⊚ | ⊚ | ⊚ | X | ○ | X | ⊚ | ⊚ | X | X |
| Example 6 | ⊚ | ⊚ | ⊚ | X | ○ | X | ⊚ | ⊚ | X | X |
| Example 7 | ⊚ | ⊚ | ⊚ | X | ○ | △ | ⊚ | ⊚ | △ | ○ |
| Example 8 | ⊚ | ⊚ | ⊚ | X | ○ | △ | ⊚ | ⊚ | ○ | ○ |
| Example 9 | ⊚ | ⊚ | ⊚ | ○ | ⊚ | ⊚ | ⊚ | ⊚ | ○ | ○ |
| Example 10 | ⊚ | ⊚ | ⊚ | ○ | ⊚ | ⊚ | ⊚ | ⊚ | ○ | ○ |
| Example 11 | ⊚ | ⊚ | ⊚ | ○ | ⊚ | ⊚ | ⊚ | ⊚ | ○ | ○ |
| Example 12 | ⊚ | ⊚ | ⊚ | X | ○ | ○ | ⊚ | ⊚ | △ | △ |
| Comparative Example 1 | X | X | X | X | X | X | X | X | X | X |

The marks in the Table indicate the following meanings:

a: chloroform, b: Diethyl Ether, c: Tetrahydrofuran
d: Methanol, e: Benzene, f: Hexane, g: Ethyl Acetate
h: Acetone, i: Dimethylformamide, j: Ethanol
⊚: Easily Soluble, ○: Soluble △: Scarcely Soluble
X: Insoluble As seen from the results set forth in Table 1, the derivatives of naphthalocyanine each containing a perfluoroalkyl group, according to this invention, are soluble in various solvents and thus useful for forming a processed film.

EXAMPLES 13 to 15

Similarly to the preceding Examples, triperfluoropropyl-bis(tripropylsiloxy) silicon naphthalocyanine (Example 13), diperfluoropropyl-bis(tributylsiloxy) silicon naphthalocyanine (Example 14) and diperfluoroethyl-bis(tributylsiloxy) silicon naphthalocyanine (Example 15) were synthesized and subjected to various analyses to identify the structures thereof.

EXAMPLE 16

On each of the substrates having different compositions as set forth in Table 2 and each having a thickness of 1.2 mm and a diameter of 130 mm, coated by spin coating process was a solution consisting of 1 part by weight of each of the derivatives of naphthalocyanine as set forth in Table 2 and 99 parts by weight of a solvent, whereby each of recording film layers was formed. The thickness of the thus formed recording film layer was measured by "Dektak 3030" (Trade Name) produced by Sloan Co. The thus prepared optical recording medium was placed on a turn table and rotated at 1800 rpm, and pulse signals of 3.7 MHz were recorded thereon within the radius range of from 40 to 60 mm by using an optical head provided with a semiconductor laser having an oscillation wavelength of 830 nm with an output of 6 mW on the surface of the substrate so that the laser beam is focused through the substrate on the recording film layer from the substrate side. Then, using a similar device, the output of a semiconductor laser on the surface of the substrate was set to 1.0 mW to reproduce the recorded signals, and the CN ratio (carrier-noise ratio) at the reproduction step was appraised. Furthermore, each of the prepared optical recording media was allowed to stand under a high temperature and high humidity condition (80° C., 90% RH) for 3000 hours, and then the CN ratio was measured. The results are shown in Table 2.

TABLE 2

| Derivative of Naphthalocyanine (ratio by weight) | Substrate* | Solvent | Thickness of film (Å) | Initial CN Ratio (dB) | CN Ratio after the Lapse of 3000 hours (dB) |
|---|---|---|---|---|---|
| Example 12 | PC | Cyclohexane | 700 | 62 | 62 |
| Example 8 | PC | Cyclohexane | 790 | 59 | 60 |
| Example 9 | PC | Cyclohexane | 760 | 62 | 60 |
| Example 10 | PC | Cyclohexane | 800 | 58 | 58 |
| Example 11 | PC | Cyclohexane | 830 | 57 | 59 |
| Example 13 | PMMA2P | Toluene | 900 | 59 | 59 |
| Exampl4 14 | PMMA2P | Toluene | 920 | 62 | 60 |
| Example 15 | PC | Ethanol | 680 | 60 | 61 |
| Example 12 | PC | Ethanol | 700 | 61 | 61 |
| Example 8 | PMMA | Ethanol | 720 | 58 | 58 |
| Example 9 | PMMA2P | Chloroform | 910 | 57 | 58 |
| Example 11 | PMMA2P | Chloroform | 890 | 59 | 57 |
| Ex. 8:Ex. 1 (7:3) | PC | Cyclohexane | 1010 | 59 | 61 |
| Ex. 15:Ex. 1 (9:2) | PC | Cyclohexane | 970 | 58 | 60 |
| Ex. 15:Ex. 1 (8:2) | PC | Cyclohexane | 950 | 61 | 60 |
| Ex. 15:Ex. 1 (7:3) | PC | Cyclohexane | 990 | 62 | 61 |

*PC: Polycarbonate Substrate. PMMA: Polymethyl Methacrylate Substrate
PMMA2P: Polymethyl Methacrylate 2P Substrate As will be seen from the results shown in Table 2, the derivatives of naphthalocyanine used to form optical recording media, according to this invention, form recording film layers having superior recording and reproducing properties on various substrates, such as polycarbonate substrate, and that the thus formed recording film layers are excellent in amorphous film retention capability under an accelerated environmental test condition.

COMPARATIVE EXAMPLE 2

A recording film layer was formed by coating, by the spin coating process similar to Example 16, a solution consisting of 1 part by weight of a compound represented by the following structural formula and 99 parts by weight of toluene on a polymethyl methacrylate 2P substrate having a thickness of 1.2 mm and a diameter of 130 mm. The thickness of the thus formed recording film layer was 1000 Å. Similarly to Example 16, recording and reproduction were effected using the thus prepared recording medium to find that the CN ratio was 39 dB and that the recording and read-out of the signals were not so satisfactory. In addition, the recording film layer was crystallized to form microcrystals to lose its reproduction capability after it was retained under a high temperature and high humidity condition (80° C., 90% RH) for 500 hours.

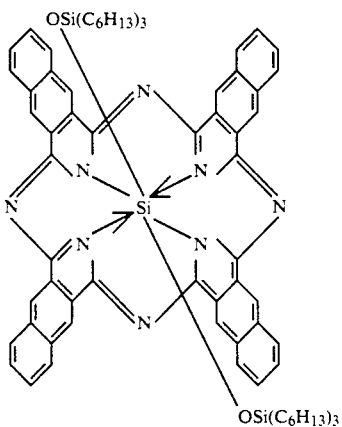

COMPARATIVE EXAMPLE 3

A recording film layer was formed by coating, by the spin coating process similar to Example 16, a solution consisting of 1 part by weight of a cyanine pigment NK-2905 (produced by Nippon Kanko Shikiso Kenkyusho) and 99 parts by weight of dichloroethane on a polymethyl methacrylate 2P substrate having a thickness of 1.2 mm and a diameter of 130 mm. The thickness of the thus formed recording film layer was 700 Å. The thus prepared recording medium was allowed to stand for 3000 hours under a high temperature and high humidity condition (80° C., 90% RH), and then the reflectivity thereof was measured to find that the reflectivity was abruptly lowered after the lapse of about 500 hours to show the lack of satisfactory durability. The CN ratio retention properties under an accelerated environmental condition was appraised by a similar procedure as described in Example 16 to find that the CN ratio was lowered to 70% of the initial CN ratio.

EXAMPLE 17

Durability to a reproducing laser beam (830 nm) of each of the optical recording media prepared in Example 16 was appraised. The appraisal test was conducted by measuring the CN ratio after repeated reproduction of $10^6$ times while setting the output of the used reproducing laser beam to 1.0 mW, 1.4 mW and 1.6 mW. The results are shown in Table 3.

TABLE 3

| Derivative of Naphthalocyanine (ratio by wt.) | Initial CN Ratio (dB) | CN Ratio after Repeated Reproduction of $10^6$ Times (dB) | | |
|---|---|---|---|---|
| | | 1.0 mW | 1.4 mW | 1.6 mW |
| Example 12 | 62 | 62 | 62 | 52 |
| Example 8 | 59 | 59 | 58 | 50 |
| Example 9 | 62 | 62 | 60 | 50 |
| Example 10 | 58 | 58 | 58 | 43 |
| Example 11 | 57 | 57 | 57 | 42 |
| Example 13 | 59 | 59 | 59 | 42 |
| Example 14 | 62 | 62 | 62 | 46 |
| Example 15 | 60 | 60 | 60 | 48 |
| Example 12 | 61 | 61 | 60 | 44 |
| Example 8 | 58 | 58 | 58 | 41 |
| Example 9 | 57 | 57 | 57 | 40 |
| Example 11 | 59 | 59 | 57 | 38 |
| Ex. 8:Ex. 1 (7:3) | 59 | 59 | 59 | 54 |
| Ex. 15:Ex. 1 (8:2) | 58 | 58 | 57 | 52 |
| Ex. 15:Ex. 1 (8:2) | 61 | 61 | 61 | 52 |
| Ex. 15:Ex. 1 (7:3) | 62 | 62 | 62 | 51 |

As will be seen from the results set forth in Table 3, it was found that the derivatives of naphthalocyanine used in the present invention could retain the initial CN ratios after the repeated reproduction of $10^6$ times at 1.4 mW, although the CN ratios were gradually lowered when an extremely intensive reproducing beam of 1.6 mW was used.

COMPARATIVE EXAMPLE 4

The durability to reproducing laser beams of the optical recording medium prepared by Comparative Example 2 was appraised similarly to Example 17. The result revealed that the CN ratio began to lower after the repeated reproduction of $10^4$ times when a reproducing laser beam of 1.0 mW was used and tracking cound not be traced after the repeated reproduction of $10^5$ times.

We claim:

1. A derivative of naphthalocyanine containing a perfluoroalkyl group and represented by the following formula (I) of;

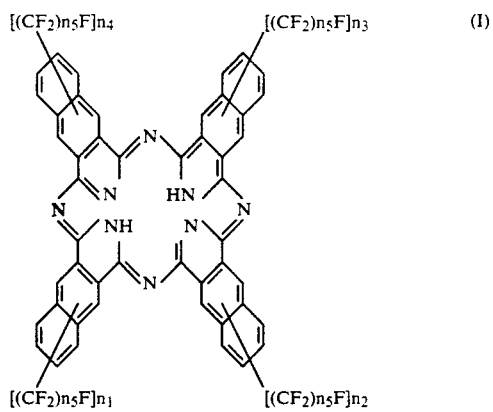

wherein $n_1$, $n_2$, $n_3$ and $n_4$ each stand for an integer of from 0 to 2, and $n_1+n_2+n_3+n_4 \neq 0$; and $n_5$ stands for an integer of from 1 to 10.

2. A derivative of naphthalocyanine containing a perfluoroalkyl group and represented by the following formula (II) of;

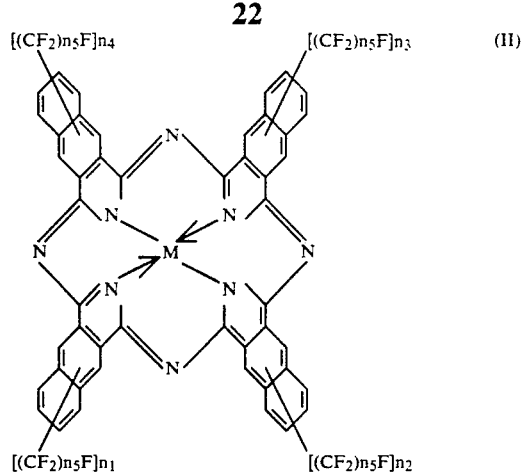
(II)
wherein M stands for $(R)_3SiO-Si-OSi(R)_3$ or $[F(CF_2)_{n_5}]-(R)_2SiO-Si-OSi(R)_3$ where R is an alkyl group having 1 to 10 carbon atoms; $n_1$, $n_2$, $n_3$ and $n_4$ each stand for an integer of from 0 to 2 and $n_5$ stands for an integer of from 1 to 10, $n_1+n_2+n_3+n_4 \neq 0$ when M is $(R)_3SiO-Si-OSi(R)_3$.
* * * * *